United States Patent
Gasper

(10) Patent No.: US 8,197,762 B2
(45) Date of Patent: Jun. 12, 2012

(54) METHOD OF DISPENSING A VOLATILE MATERIAL

(75) Inventor: Thomas P. Gasper, Germantown, WI (US)

(73) Assignee: S.C. Johnson & Son, Inc., Racine, WI (US)

(*) Notice: Subject to any disclaimer, the term of this patent is extended or adjusted under 35 U.S.C. 154(b) by 381 days.

(21) Appl. No.: 12/565,550

(22) Filed: Sep. 23, 2009

(65) Prior Publication Data

US 2010/0078498 A1 Apr. 1, 2010

Related U.S. Application Data

(60) Provisional application No. 61/194,618, filed on Sep. 29, 2008.

(51) Int. Cl.
| | |
|---|---|
| A61L 9/00 | (2006.01) |
| G05B 17/00 | (2006.01) |
| A62B 7/08 | (2006.01) |
| B65D 5/00 | (2006.01) |
| B67D 5/22 | (2006.01) |
| B67D 5/62 | (2006.01) |
| F24F 13/00 | (2006.01) |
| A24F 25/00 | (2006.01) |
| F24H 7/00 | (2006.01) |
| G01F 1/68 | (2006.01) |
| G07F 11/00 | (2006.01) |

(52) U.S. Cl. ........... 422/125; 422/1; 422/3; 422/5; 422/116; 422/119; 422/124; 422/306; 222/3; 222/37; 222/52; 222/638; 222/146.5; 454/236; 454/229; 454/237; 239/13; 239/34; 239/136; 392/340; 392/387; 73/9; 73/204.18; 73/204.19; 221/9; 221/15

(58) Field of Classification Search ............ 422/1, 3, 422/5, 116, 119, 124–125, 306; 222/3, 37, 222/52, 638, 146.5; 454/236, 229, 237; 239/13, 239/34, 136; 392/340, 387; 73/9, 204.18, 73/204.19; 221/9, 15
See application file for complete search history.

(56) References Cited

U.S. PATENT DOCUMENTS

| | | | |
|---|---|---|---|
| 3,410,488 A | 11/1968 | Sugimura |
| 3,948,445 A | 4/1976 | Andeweg |
| 4,425,302 A | 1/1984 | Pons Pons |
| 4,603,030 A | 7/1986 | McCarthy |
| 4,849,606 A | 7/1989 | Martens, III et al. |
| 4,924,068 A | 5/1990 | Henri |
| 5,029,729 A | 7/1991 | Madsen et al. |

(Continued)

FOREIGN PATENT DOCUMENTS

JP 5173648 7/1993

(Continued)

OTHER PUBLICATIONS

U.S. Appl. No. 12/319,606.

(Continued)

*Primary Examiner* — Jill Warden
*Assistant Examiner* — Monzer Chorbaji

(57) ABSTRACT

A method of dispensing a volatile material comprises the steps of providing power to a volatile material diffuser having a diffusion element. The method further includes the step of operating the diffusion element for a randomly determined period of time, wherein the diffusion element is continuously activated and deactivated during the period of time at a randomly determined duty cycle.

11 Claims, 7 Drawing Sheets

U.S. PATENT DOCUMENTS

| | | | |
|---|---|---|---|
| 5,111,477 A | 5/1992 | Muderlak | |
| 5,175,791 A | 12/1992 | Muderlak et al. | |
| 5,297,988 A * | 3/1994 | Nishino et al. | 454/75 |
| 5,591,395 A | 1/1997 | Schroeder et al. | |
| 5,591,409 A | 1/1997 | Watkins | |
| 5,647,053 A | 7/1997 | Schroeder et al. | |
| 5,937,140 A | 8/1999 | Leonard et al. | |
| 6,204,623 B1 | 3/2001 | Levy et al. | |
| 6,390,453 B1 | 5/2002 | Frederickson et al. | |
| 6,478,440 B1 | 11/2002 | Jaworski et al. | |
| 6,581,915 B2 | 6/2003 | Bartsch et al. | |
| 6,603,924 B2 | 8/2003 | Brown et al. | |
| 6,661,967 B2 | 12/2003 | Levine et al. | |
| 6,712,287 B1 | 3/2004 | Le Pesant et al. | |
| 6,790,408 B2 | 9/2004 | Whitby et al. | |
| 6,792,199 B2 | 9/2004 | Levine et al. | |
| 6,854,717 B2 | 2/2005 | Millan | |
| 6,857,580 B2 | 2/2005 | Walter et al. | |
| 6,862,403 B2 | 3/2005 | Pedrotti et al. | |
| 6,917,754 B2 | 7/2005 | Pedrotti et al. | |
| 6,920,282 B2 | 7/2005 | He et al. | |
| 6,923,383 B1 | 8/2005 | Joshi et al. | |
| 6,931,202 B2 | 8/2005 | Pedrotti et al. | |
| 6,996,335 B2 | 2/2006 | Zobele | |
| 7,036,800 B2 | 5/2006 | Ellis | |
| 7,223,361 B2 | 5/2007 | Kvietok et al. | |
| 7,249,719 B2 | 7/2007 | He et al. | |
| 7,484,716 B2 | 2/2009 | Morie et al. | |
| 7,493,028 B2 | 2/2009 | DeWitt et al. | |
| 2004/0101447 A1 | 5/2004 | Tajima et al. | |
| 2006/0193611 A1 | 8/2006 | Ruiz Ballesteros et al. | |
| 2007/0012718 A1 | 1/2007 | Schramm et al. | |
| 2007/0166185 A1 | 7/2007 | Bartels | |
| 2007/0166186 A1 | 7/2007 | Stec | |
| 2007/0280653 A1 | 12/2007 | Viera | |
| 2008/0014125 A1 | 1/2008 | He et al. | |
| 2008/0095522 A1 | 4/2008 | Deflorian et al. | |
| 2008/0191370 A1 | 8/2008 | Pankhurst et al. | |

FOREIGN PATENT DOCUMENTS

| | | |
|---|---|---|
| WO | 2004093929 A2 | 11/2004 |
| WO | WO 2004/093929 A2 * | 11/2004 |
| WO | 2006110794 A1 | 10/2006 |
| WO | WO 2006/110794 A1 * | 10/2006 |
| WO | WO2007064189 | 6/2007 |
| WO | WO2007079046 | 7/2007 |
| WO | 2008119068 A1 | 10/2008 |
| WO | WO 2008/119068 A1 * | 10/2008 |
| WO | WO2008149065 | 12/2008 |

OTHER PUBLICATIONS

PCT/US2009/005364 International Search Report and Written Opinion dated Nov. 26, 2009.

* cited by examiner

US 8,197,762 B2

METHOD OF DISPENSING A VOLATILE MATERIAL

CROSS REFERENCE TO RELATED APPLICATIONS

This application claims the benefit of U.S. Provisional Application No. 61/194,618, filed Sep. 29, 2008, the disclosure of which is incorporated herein by reference in its entirety.

REFERENCE REGARDING FEDERALLY SPONSORED RESEARCH OR DEVELOPMENT

Not applicable

SEQUENTIAL LISTING

Not applicable

BACKGROUND

1. Field of the Invention

The present invention relates to methods of dispensing volatile materials, and more particularly, to methods of dispensing volatile material according to pre-established programming that aids in diminishing or preventing habituation.

2. Description of the Background

A multitude of volatile material diffusion devices or diffusers exist in the marketplace. Many of such devices are passive devices that require only ambient air flow to disperse the liquid active material therein. Other devices are battery-powered or receive household power via a plug extending from the device. A cord may be coupled between the plug and the device, or the plug may be mounted directly on the device.

Various means for dispensing volatile materials from volatile material diffusers are also known in the art. For example, some diffusers include a heating element for heating a volatile material to promote vaporization thereof. Other diffusers employ a fan or blower to generate air flow to direct volatile material out of the diffuser into the surrounding environment. In another type of diffuser, one or more volatile materials may be emitted from the diffuser using a bolus generator that delivers a pulse of air to eject a scent ring. Still other diffusers that dispense volatile materials utilize ultrasonic means to dispense the volatile materials therefrom. In addition, other diffusers utilize more than one of these means to vaporize and/or disperse volatile materials.

A problem with past volatile material diffusers is that a user may become accustomed to or habituated to a particular volatile material. Habituation is a phenomenon that occurs when a person becomes use to a particular volatile material or fragrance such that they no longer perceive the volatile material. Various diffusers have attempted to alleviate this problem. Some diffusers include a switch or other mechanism that is controlled by the user, whereby the user can change the intensity level at which the volatile material is dispensed. The manner in which the intensity level of the volatile material is varied is either mechanical or electrical in nature.

Other diffusers include one or more containers having a volatile material therein, wherein a fan and/or a heater is periodically actuated to dispense the volatile material at particular time intervals.

Still other diffusers include at least two fragrances that are emitted in an alternating sequence. One such diffuser includes a housing having first and second heaters, wherein the housing is adapted to releasably secure first and second containers having first and second wicks respectively extending therefrom. The wicks are disposed adjacent the heaters and the heaters are turned on and off in an alternating sequence to alternately emit the first and second fragrances.

SUMMARY OF THE INVENTION

According to one aspect of the present invention, a method of dispensing a volatile material includes the step of providing power to a volatile material diffuser having a diffusion element. The method further includes the step of operating the diffusion element for a randomly determined period of time, wherein the diffusion element is continuously activated and deactivated during the period of time at a randomly determined duty cycle.

According to a further aspect of the present invention, a method of dispensing a volatile material includes the steps of providing power to a volatile material diffuser having a diffusion element, operating the diffusion element for a first randomly determined period of time, wherein during the first period of time, the diffusion element has a first characteristic. The method further includes the step of operating the diffusion element for a second randomly determined period of time after the first period of time has elapsed, wherein during the second period of time, the diffusion element has a second characteristic.

According to yet another aspect of the present invention, a method of dispensing a volatile material includes the steps of providing power to a volatile material diffuser having a diffusion element and automatically generating a first random number, N1, and a second random number, N2. The method further includes the step of operating the diffusion element for a period of time determined by multiplying N1 by a time factor, wherein the diffusion element is continuously activated and deactivated during the period of time for a duty cycle defined by multiplying N2 by a percent factor.

Other aspects and advantages of the present invention will become apparent upon consideration of the following detailed description and the attached drawings, in which like elements are assigned like reference numerals.

DETAILED DESCRIPTION

Figure 1:
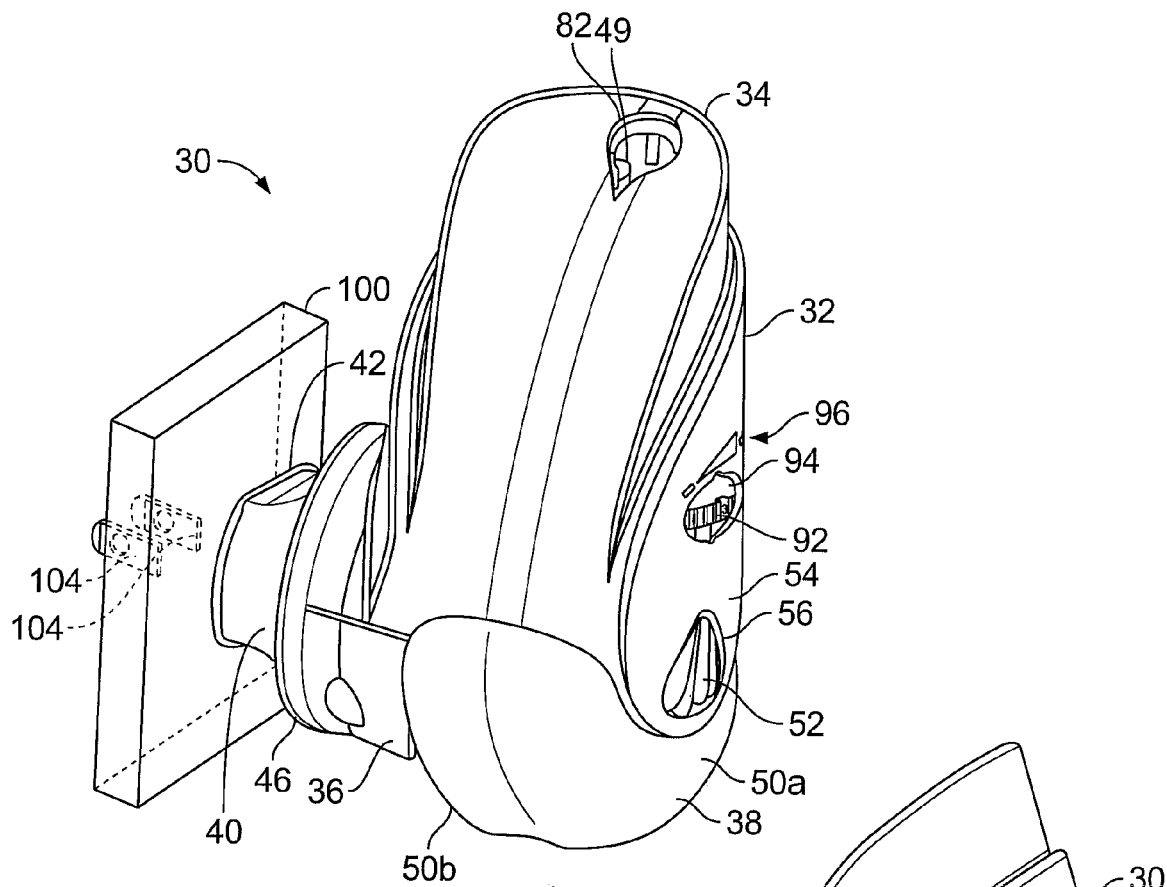
FIG. 1 is a perspective view of a volatile material diffuser according to the present invention.
Figure 2:
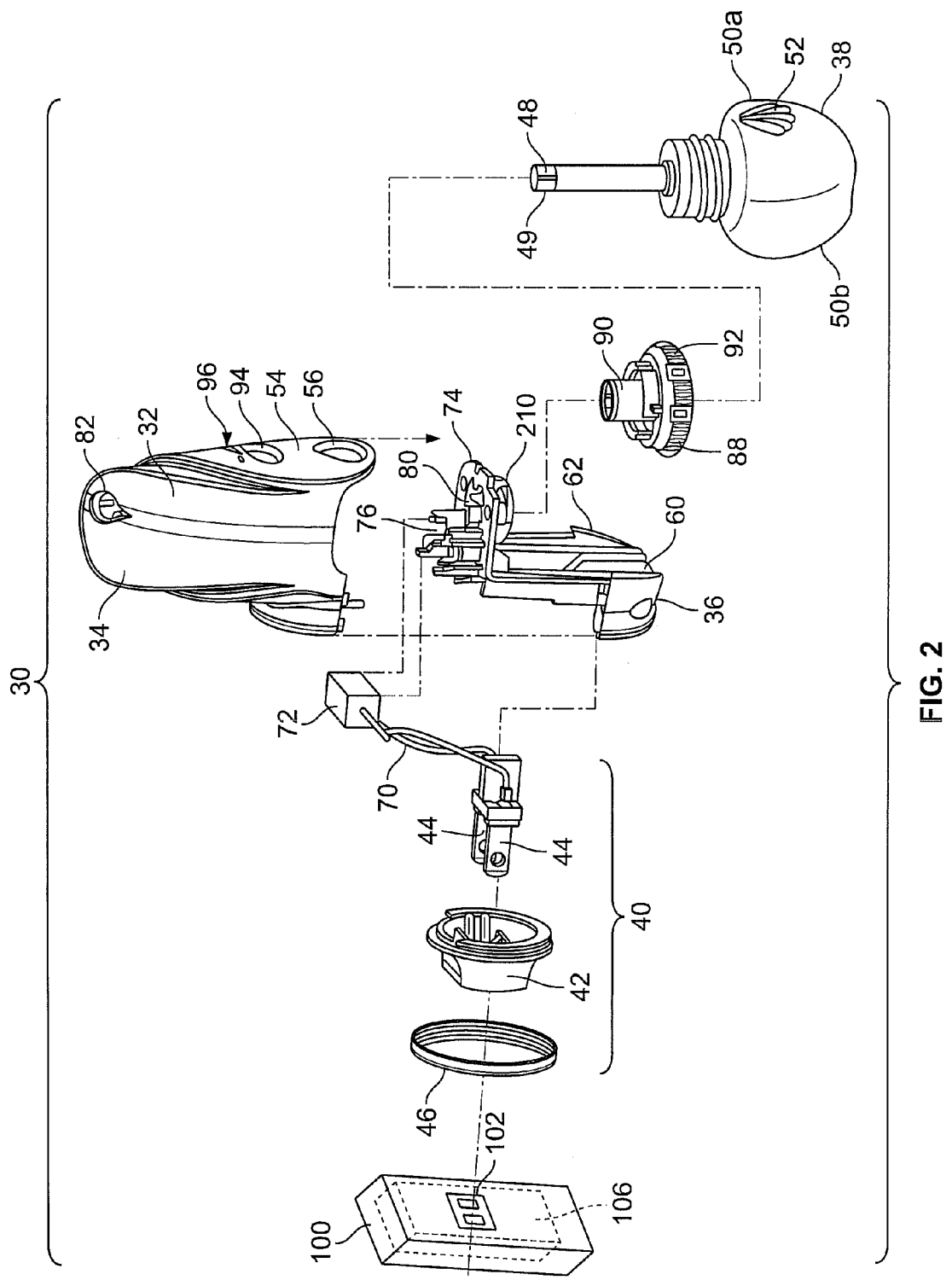
FIG. 2 is an exploded view of the volatile material diffuser of FIG. 1.

Referring to FIGS. 1 and 2, a volatile material diffuser 30 generally includes a multi-piece housing 32 having an upper housing portion 34 and a lower housing portion 36 fastened together by heat-staking or other suitable fastening means, including, for example, rivets, press fit, snap fit, screws, ultrasonic welding, adhesives, and the like. A container 38 is detachably retained within the lower housing portion 36. The diffuser 30 further includes an electrical plug assembly 40 having a plug portion 42 rotatably secured between the upper and lower housing portions 34, 36 and electrical contacts 44 extending outwardly from the plug portion 42 for insertion into a conventional wall outlet (not shown) or other electronic device, as discussed in greater detail hereinafter. A collar 46 is disposed over the plug portion 42 to ensure proper engagement of the upper and lower housing portions 34, 36 around the plug portion 42.

Figure 3:
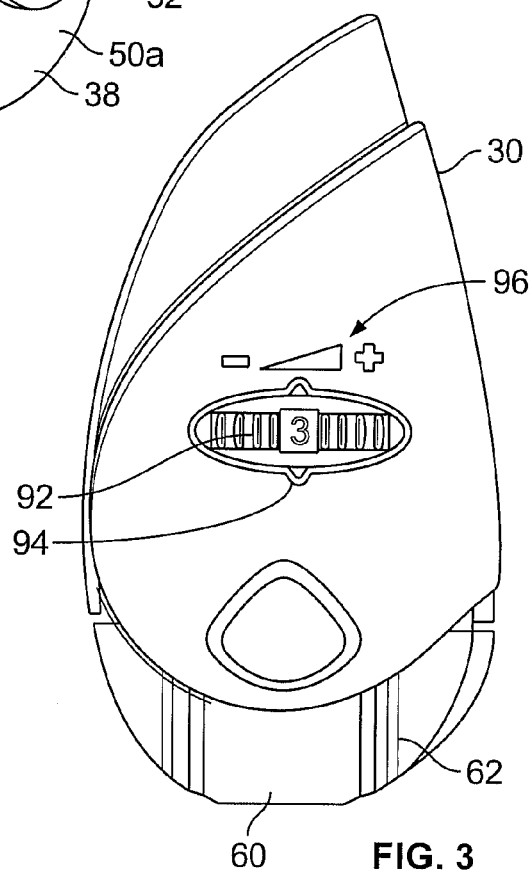
FIG. 3 is a front elevational view of the volatile material diffuser of FIG. 1.

The container 38 includes a volatile material disposed therein and a wick 48 in contact with the volatile material and extending out of the container 38. The wick 48 is adapted to draw the volatile material in the form of a liquid out of the container 38 toward an upper portion 49 of the wick 48. The container 38 is adapted for insertion into and securement within the housing 32. In particular, front and rear surfaces 50a, 50b of the container 38 include shell-shaped protrusions 52 (only the shell-shaped protrusion on the front surface 50a is shown) extending therefrom. The container 38 is inserted into the lower housing portion 36 by inserting the wick 48 into the housing 32 and thereafter moving the container 38 upwardly. As the container 38 is moved upwardly, the shell-shaped protrusion 52 on the front surface 50a of the container 38 causes a slight outward deformation of a front wall 54 of the upper housing portion 34 to allow the protrusion 52 to pass into a similarly-shaped aperture 56 in the front wall 54 of the upper housing portion 34. As the container 38 is moved upwardly, the shell-shaped protrusion (not shown) on the rear surface 50b of the container 38 moves along a groove 60 formed in a front surface 62 of the lower housing portion 36, as seen in FIGS. 2 and 3. As the shell-shaped protrusion 52 on the front surface 50a of the container 38 snaps into the aperture 56, a top portion of the shell-shaped protrusion (not shown) on the rear surface 50b of the container 38 comes to rest at a top portion of the groove 60 that has a shape similar to a top portion of the shell-shaped protrusion. Pulling the container 38 in a downward direction causes a slight outward deformation of the front wall 54 of the upper housing portion 34 to allow a user to remove and replace the container 38.

Although the container 38 is shown as being secured within the housing 32 by shell-shaped protrusions 52, a neck portion of the container 38 may alternatively be designed to snap or screw into the housing 32.

The volatile material within the container 38 may be any type of volatile material, for example, an insecticide, an insect repellant, an insect attractant, a disinfectant, a mold or mildew inhibitor, a fragrance, a disinfectant, an air purifier, an aromatherapy scent, an antiseptic, an odor eliminator, a positive fragrancing volatile material, an air-freshener, a deodorizer, or the like, and combinations thereof.

Referring to FIG. 2, the electrical contacts 44 are electrically connected via conventional electrical conductors 70, such as wires or electrodes, to a heating device 72. The lower housing portion 36 includes a horizontal platform 74 extending generally perpendicularly from the front surface 62 of the lower housing portion 36. A heating device support 76 extends upwardly from the platform 74 for holding the heating device 72. When the container 38 is inserted into the diffuser 30, the wick 48 thereof extends through a channel 80 in the platform 74 such that the top portion 49 of the wick 48 is disposed adjacent the heating device 72. The heating device 72 applies heat to the wick 48 to enhance the rate at which the volatile material therein is evaporated. As volatile material is evaporated from the wick 48, the volatile material moves upwardly and out an aperture 82 disposed in the upper housing portion 34.

The diffuser 30 further includes an adjustment mechanism 88 that positions an upper portion of the wick 48 in one of a number of discrete positions relative to the heating device 72 to change the intensity at which the volatile material is evaporated. The adjustment mechanism 88 includes a hollow cylindrical portion 90 that surrounds and engages the upper portion of the wick 48 to move same toward and away from the heating device 72. The adjustment mechanism 88 is similar to the adjustment mechanism described in Pedrotti et al. U.S. Pat. No. 6,931,202, the disclosure of which is hereby incorporated by reference in its entirety. A dial portion 92 is provided for rotating the cylindrical portion 90 to change the intensity at which the volatile material is evaporated. The dial portion 92 extends through an opening 94 in the front wall 54 of the upper housing portion 34 such that a user can rotate the dial portion 92. An indicator 96 is preferably disposed on the front wall 54 of the upper housing portion 34 to provide an indication to a user of how to rotate the dial portion 92 to increase and decrease an intensity at which the volatile material is evaporated.

The diffuser 30 described with respect to FIGS. 1-3 is described in greater detail in Zobele U.S. Pat. No. 6,996,335, the disclosure of which is incorporated herein in its entirety.

Referring again to FIGS. 1 and 2, the diffuser 30 includes an adapter box 100 having a conventional electrical socket 102 therein (FIG. 2), wherein the electrical contacts 44 extending from the plug portion 42 of the diffuser 30 are inserted into and retained within the electrical socket 102. The adapter box 100 includes a set of electrical contacts 104 extending therefrom for insertion into a conventional wall socket (not shown) to power the diffuser 30. The adapter box 100 includes a printed circuit board (PCB) 106 (FIG. 2) disposed therein for controlling the functionality of the heating device 72, as discussed in greater detail hereinafter. The adapter box 100 may be used with any diffuser known in the art. Optionally, the adapter box 100 may be replaced by a PCB 106 that implements the same or similar functionality and which is disposed within the diffuser 30.

Figure 4:
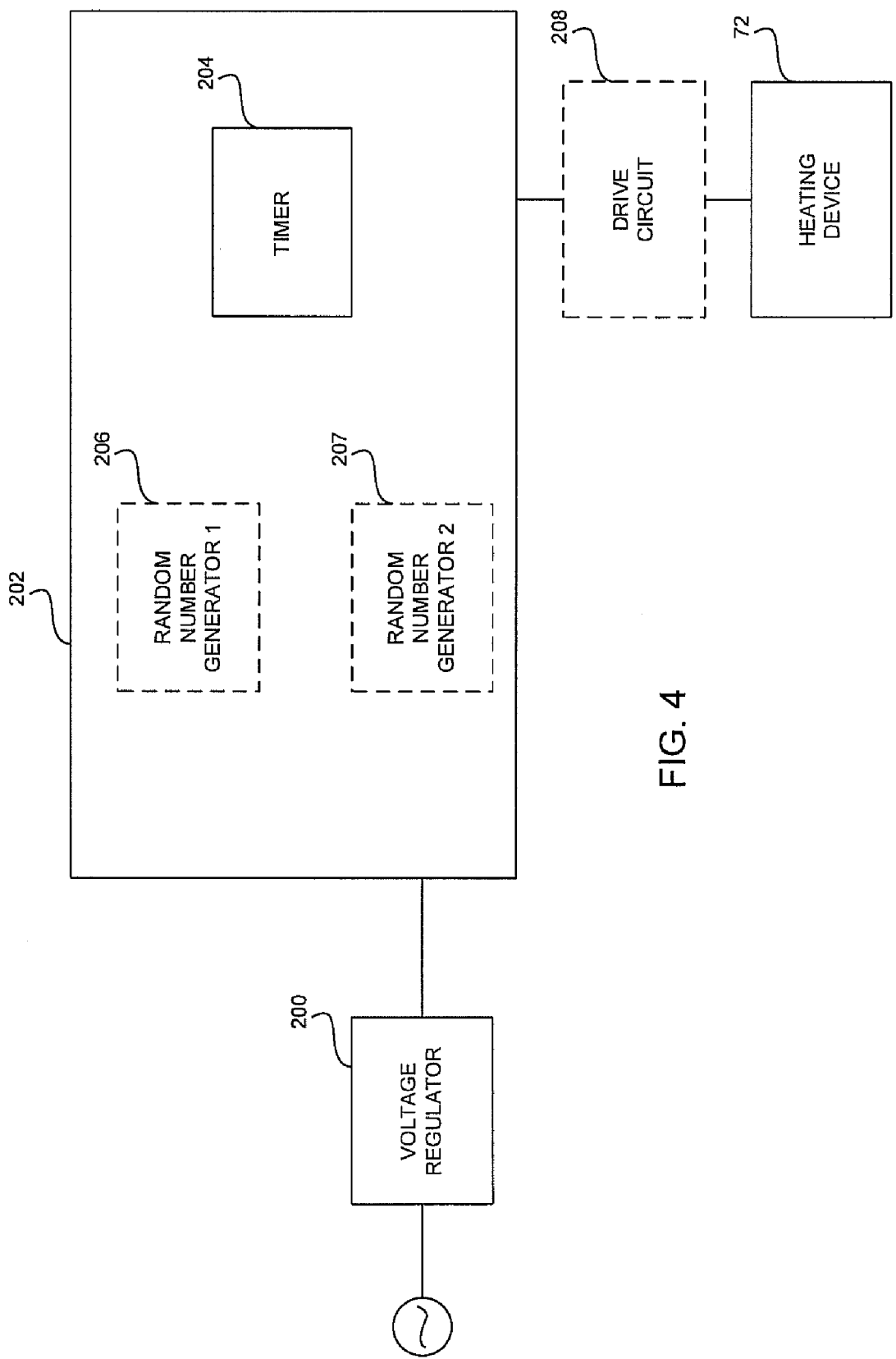
FIG. 4 is a block diagram of circuits including a programmable device for controlling application of power to a heating device of the diffuser of FIGS. 1-3.

FIG. 4 depicts a block diagram of circuits for controlling the operation of the heating device 72 of the volatile material diffuser 30. The circuits of FIG. 4 are carried by, for example, the PCB 106. A voltage regulator 200 known to those of ordinary skill in the art provides a regulated voltage Vcc to a programmable device 202. In one embodiment, the programmable device 202 is an 8-pin flash based 8-bit CMOS microcontroller PIC12F629 sold by Microchip Technology Inc. of Chandler, Ariz. The programmable device 202 includes a timer 204, a first random number generator 206, and a second random number generator 207. An optional drive circuit 208 is connected between the programmable device 202 and the heating device 72. The optional drive circuit 208 may be carried by the PCB 106 and is utilized if the programmable device 202 cannot develop suitable power to operate the heating device 72.

Figure 4A:
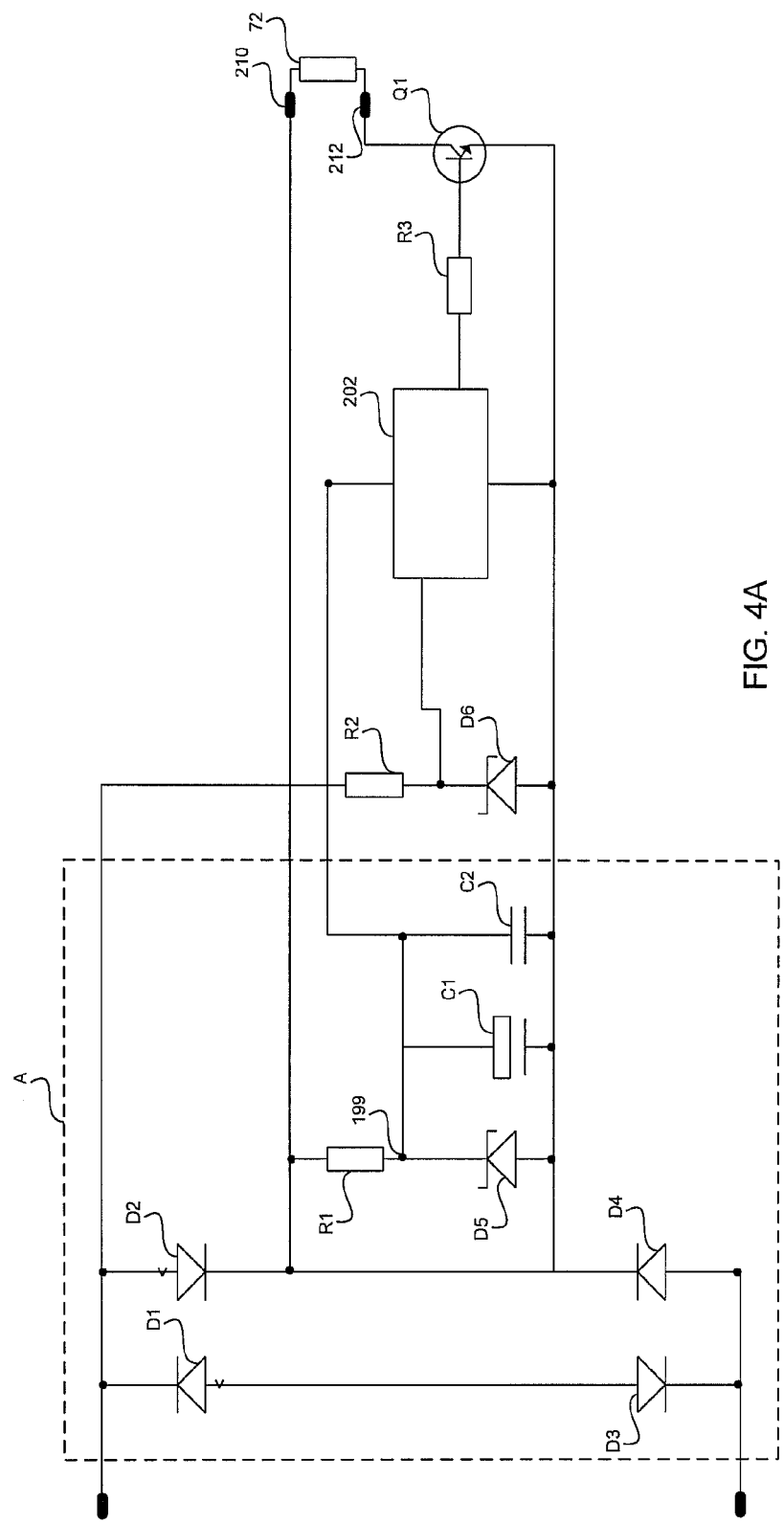
FIG. 4A is a schematic of one embodiment of the circuits of FIG. 4.

FIG. 4A illustrates one embodiment of the circuits of FIG. 4, wherein the voltage regulator 200 is shown in a block A. The block A includes four diodes D1-D4 coupled in a full bridge configuration to develop a full wave rectified voltage from a 120 VAC power supply. A resistor R1 and a zener diode D5 are connected in parallel across the full wave rectified voltage and first and second capacitors C1 and C2 are connected in parallel between a terminal 199 and ground for filtering purposes. The components R1, D5, C1, and C2 together develop a 5V voltage for the programmable device 202. A zero-crossing of the A.C. voltage input is sensed by circuitry comprising a resistor R2 and a zener diode D6 to provide a timing reference to the programmable device 202. An output of the programmable device provides a control signal via a resistor R3 to a base of a transistor Q1. The collector of the transistor Q1 is connected to a first terminal 210 of the heating device 72 and an emitter of the transistor Q1 is connected to ground. A second terminal 212 of the heating device 72 is connected to the full wave rectified voltage. The programmable device 202 controls how much of each pulse of the full wave rectified voltage that is applied to the heating device 72 by turning the transistor Q1 on and off for a predetermined amount of time during each pulse of the full wave rectified voltage. While this is not a conventional implementation of pulse width modulation (PWM), the conduction time of the heating device 72 is varied as if a PWM signal were applied thereto.

In operation, the programmable device 202 senses the zero crossing of the A.C. power supply once every 8 milliseconds. The programmable device 202 is programmed to save parameters, such as how much time has elapsed since the timer 204 was activated, when the programmable device 202 determines that the diffuser 30 has been disconnected form the A.C. power supply. Specifically, when the diffuser 30 is disconnected from the A.C. power supply, the programmable device 202 saves current parameters because the programmable device 202 does not sense the zero-crossing for a period of more than 8 milliseconds while the capacitors C1 and C2 discharge. The programmable device 202 subsequently restores the saved parameters when power is reapplied to the diffuser 30 and the programmable device 202 senses the zero crossing.

Figure 5:
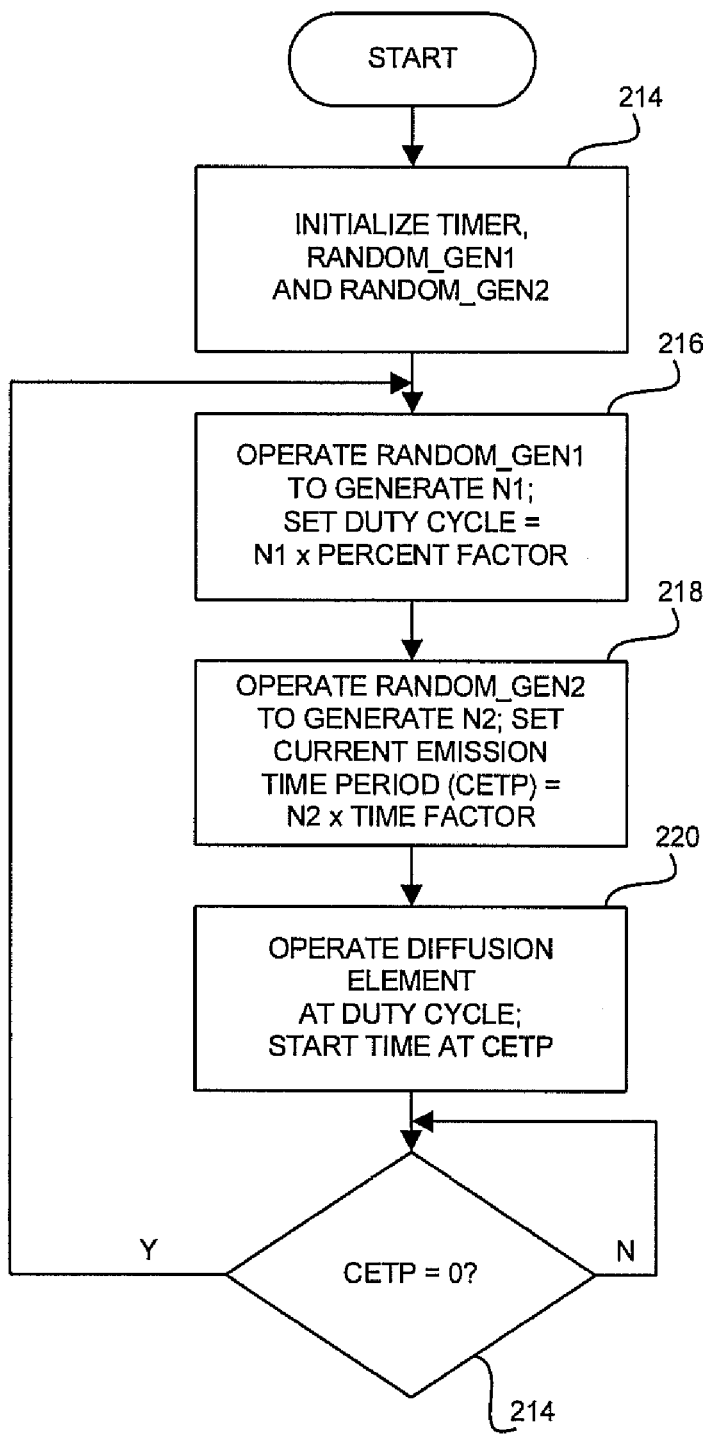
FIG. 5 depicts a flow chart illustrating one embodiment of programming that may be implemented by a programmable device for operation of the heating device of the diffuser of FIGS. 1-3 or any other diffusion element.

FIG. 5 illustrates a first mode of operation that may be implemented by a programmable device that controls any diffusion element, such as the programmable device 202 that controls operation of the heating device 72. Operation begins at a block 214 after the adapter box 100 or diffuser 30 is plugged into an electrical outlet, wherein the block 214 initializes the timer 204 and the first and second random number generators 206, 207. Following the block 214, control passes to a block 216 that operates the first random number generator 206 to generate a number N1. The block 216 also sets a duty cycle (an on or active time of the diffusion element divided by the total period, which includes the on and an off time) for the diffusion element, such as heating device 72, to:

$$\text{DUTY CYCLE}=N1 \times \text{PERCENT FACTOR} \quad [1]$$

Thereafter, control passes to a block 218 that operates the second random number generator 207 to generate a number N2 and thereafter sets the timer 204 to a period of:

$$\text{CURRENT EMISSION TIME PERIOD (CETP)} = N2 \times \text{TIME FACTOR} \quad [2]$$

A block 220 operates the diffusion element, such as the heating device 72, at the duty cycle and starts the timer 204 at the current emission time period (counting down). During such current emission time period, the diffusion element is continuously activated and deactivated according to the duty cycle.

Following the block 220, a block 222 determines if the current emission time period has elapsed. Control remains with the block 222 until the current emission time period has elapsed. Once the block 222 determines that the current emission time period has elapsed, control returns to the block 216 where the first random number generator 206 generates a number N1 and operation continues to cycle through the loop of FIG. 5 including blocks 216, 218, 220, 222 until power is no longer provided to the adapter box 100 or diffuser 30.

In an exemplary embodiment, the diffuser 30 of FIGS. 1-4A was utilized to test the programming of FIG. 5. In such embodiment, the percent factor was set to 10% and the time factor was set to 1 hour. During each cycle through the blocks 216, 218, 220, and 222 of FIG. 5, N1 was randomly selected between and including 1 and 10, such that the resultant duty cycle was between 10% and 100% and N2 was randomly selected between and including 6 and 12, such that a particular duty cycle operates for a current emission time period between 6 hours and 12 hours.

Figure 6:
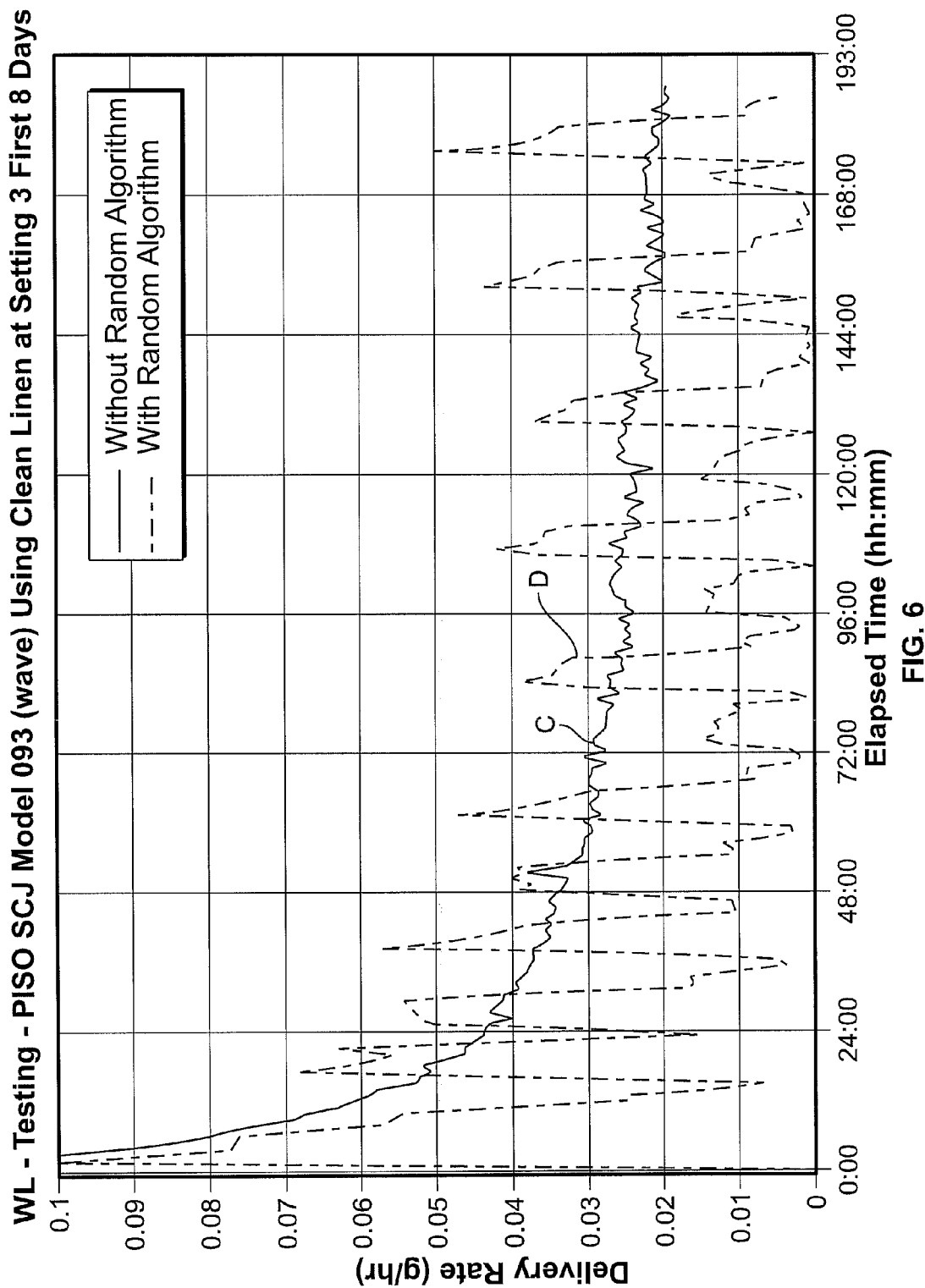
FIG. 6 is a plot depicting delivery rate versus time for a sample testing cycle of the programming depicted in FIG. 5.

With reference to FIG. 6, a plot of the delivery rate (grams/hour) versus time (hours) for this sample running of the programming of FIG. 5 illustrates an advantage that is derived from such programming to control the heating device 72. A solid line C represents a delivery rate of the heating device 72 when the heating device 72 is operated at a duty cycle of 100% over a period of 193 hours. As seen in FIG. 6, the delivery rate shown by the solid line C steadily decreases over time. In contrast, a broken line D illustrates the delivery rate of the heating device 72 when the duty cycle of the heating device 72 is varied over time according to one example of the programming of FIG. 5. Unlike the delivery rate shown by the solid line C, the delivery rate illustrated by the broken line D indicates spikes in the delivery rate each time a different duty cycle is applied to the heating device 72 according to the programming of FIG. 5.

Although one specific embodiment of the equations for determining the current emission time period and the duty cycle of equations [1] and [2] is disclosed herein, a number of variations are possible. For example, the percent factor is preferably set to any percentage between about 1% and about 99%, more preferably between about 5% and about 20%, and most preferably about 10%. The percent factor may also be set to a fractional percentage. Still further, the time factor is preferably set to any time period between about 10 seconds and about 8 hours, more preferably between about 1 minute and 2 hours, and most preferably between about 5 minutes and about 1 hour. The time factor may also be set to a fractional time period (e.g. 6.2 minutes).

Any range of numbers for N1 may be utilized, including fractional numbers. The range for N1 is preferably between 0 and 100, and more preferably between 1 and 10. Further, any range of numbers for N2 may be utilized that would provide enough variation in the emission of the volatile material to reduce, minimize, or prevent habituation.

As noted above, the diffusion element of the first mode of operation (FIG. 5) is continuously activated and deactivated according to randomly selected duty cycles. The total periods defining the randomly determined duty cycles herein may be the same or different for each current emission time period (CETP). The total periods are preferably greater than 0 seconds and less than the CETP, more preferably between about $\frac{1}{10}$ second and about ($\frac{1}{2} \times$ CETP), and most preferably between about 1 second and about ($\frac{1}{10} \times$ CETP).

Figure 7:
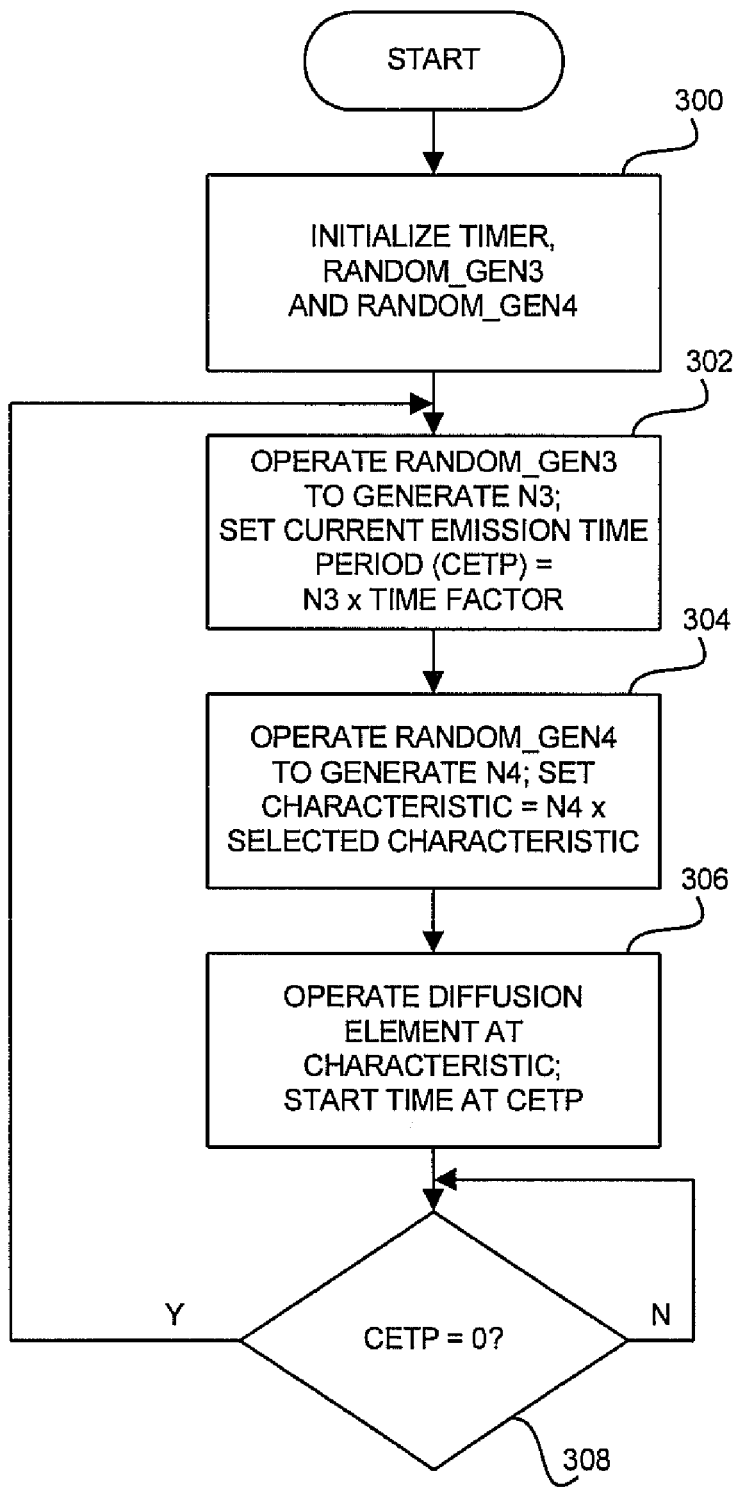
FIG. 7 depicts a flow chart illustrating a further embodiment of programming that may be implemented by the programmable device for operation of the heating device of the diffuser of FIGS. 1-3 or any other diffusion element.

FIG. 7 illustrates a second mode of operation that is implemented by a programmable device, such as the programmable device 202, to control operation of the heating device 72, or optionally any diffusion element. Operation begins at a block 300 after the diffuser is plugged into an electrical outlet, wherein the block 300 initializes a timer and third and fourth random number generators. Following the block 300, control passes to a block 302 that operates the third random number generator to generate a random number N3. The block 302 also sets the timer to a period of

CURRENT EMISSION TIME PERIOD=N3×TIME FACTOR  [3]

Thereafter, control passes to a block 304 that operates the fourth random number generator to generate a number N4 and thereafter sets a characteristic of the diffusion element based on the following equation:

CHARACTERISTIC OF DIFFUSION ELEMENT=N4×SELECTED CHARACTERISTIC  [4]

A block 306 operates the diffusion element, such as the heating device 72, at the characteristic and starts the timer at the current emission time period (counting down).

Following the block 306, a block 308 determines if the current emission time period has elapsed. Control remains with the block 308 until the current emission time period has elapsed. Once the block 308 determines that the current emission time period has elapsed, control returns to the block 302 where the third random number generator generates a number N3 and operation continues to cycle through the loop of FIG. 7 including blocks 302, 304, 306, 308 until power is no longer provided to the diffuser.

A characteristic may be any feature of any diffusion element that may be altered to aid in diminishing or preventing habituation. Various characteristics include, but are not limited to speed, intensity, temperature, frequency of actuation, length of actuation, duty cycle, and the like. Further, N4 is determined according to the characteristic and the appropriate range for such characteristic. Optionally, more than one characteristic may be set for a particular diffusion element and/or if more than one type of diffusion element is present in a diffuser, different characteristics may be set for the different diffusion elements and/or if two or more of the same type of diffusion element are present within a diffuser, different characteristics may be set for each of the diffusion elements.

Diffusion element(s) as referred to herein may be any type of element that promotes diffusion of a volatile material. Examples of diffusion elements include, but are not limited to, aerosol actuators, piezoelectric elements, heaters, fans, nebulizers, and the like. To that effect, any of the modes of operation disclosed herein may be utilized with any type of diffusion element and/or combinations of diffusion elements (e.g. a device that utilizes multiple heaters and a single fan, a device that utilizes a heater to diffuse a first volatile material and a fan to diffuse a second material, etc.).

Although the programming as disclosed herein is described as being implemented within the programmable device 202 of the diffuser 30 of FIGS. 1-3, such programming may be implemented in any plug-in type diffuser, including diffusers that emit more than one volatile material. For example, the programming described herein may be implemented in diffusers such as those described in Schroeder et al. U.S. Pat. No. 5,647,053, Schroeder et al. U.S. Pat. No. 5,591,395, Pedrotti et al. U.S. Pat. No. 6,931,202, Pedrotti et al. U.S. Pat. No. 6,862,403, Walter et al. U.S. Pat. No. 6,857,580, Pedrotti et al. U.S. Pat. No. 6,917,754, Martens III, et al. U.S. Pat. No. 4,849,606, Leonard et al. U.S. Pat. No. 5,937,140, and Jaworski et al. U.S. Pat. No. 6,478,440, Porchia et al. U.S. application Ser. No. 11/427,714, and Neumann et al. U.S. application Ser. No. 12/319,606, the disclosures of which are incorporated herein in their entirety. Further, such programming may be incorporated into any plug-in type diffusers known in the art that employ a heater.

INDUSTRIAL APPLICABILITY

The present invention provides a method of dispensing a volatile material, wherein the volatile material is emitted according to pre-established programming that seeks to reduce, minimize, or prevent habituation to the volatile material by the user.

Numerous modifications will be apparent to those skilled in the art in view of the foregoing description. Accordingly, this description is to be construed as illustrative only and is presented for the purpose of enabling those skilled in the art to make and use the present invention and to teach the best mode of carrying out same. All patents and other references cited herein are incorporated by reference in their entirety. The exclusive rights to all modifications which come within the scope of the appended claims are reserved.

I claim:

1. A method of dispensing a volatile material, the method comprising the steps of:
   providing power to a volatile material diffuser having a diffusion element; and
   operating the diffusion element for a first randomly determined period of time, wherein the diffusion element is continuously activated and deactivated during the period of time at a first randomly determined duty cycle, wherein the first randomly determined duty cycle is determined by the equation N1×PERCENT FACTOR, and wherein the PERCENT FACTOR is between 1% and 99%.

2. The method of claim 1, further including the step of operating the diffusion element for a second randomly determined period of time after the first randomly determined period of time has elapsed, wherein the diffusion element is continuously activated and deactivated during the second period of time at a second randomly determined duty cycle.

3. The method of claim 1, wherein the diffusion element is a heater.

4. The method of claim 1, wherein the first randomly determined period of time is determined by the equation N2×TIME FACTOR.

5. The method of claim 4, wherein the TIME FACTOR is between about 10 seconds and 8 hours.

6. The method of claim 5, wherein the TIME FACTOR is 1 hour and N2 is selected from an integer between and including 6 and 12.

7. The method of claim 1, wherein the PERCENT FACTOR is 10% and N1 is selected from between and including 1 and 10.

8. A method of dispensing a volatile material, the method comprising the steps of:
   providing power to a volatile material diffuser having a diffusion element;
   automatically generating a first random number, N1, and a second random number, N2; and
   operating the diffusion element for a period of time determined by multiplying N2 by a time factor, wherein the diffusion element is continuously activated and deactivated during the period of time for a duty cycle defined by multiplying N1 by a percent factor wherein the percent factor is 10% and N1 is selected from between and including 1 and 10.

9. The method of claim 8, wherein the diffusion element is a heater.

10. The method of claim 9, wherein the time factor is between about 10 seconds and about 8 hours.

11. The method of claim 10, wherein the time factor is 1 hour and N2 is selected from an integer between and including 6 and 12.

* * * * *